United States Patent
Coe et al.

(10) Patent No.: US 7,499,757 B2
(45) Date of Patent: Mar. 3, 2009

(54) ABSORBABLE MYOCARDIAL LEAD FIXATION SYSTEM

(75) Inventors: M. Sean Coe, Plymouth, MN (US); Ronald W. Heil, Jr., Roseville, MN (US); Peter T. Kelley, Buffalo, MN (US); Jason Alan Shiroff, Shoreview, MN (US); Randy W. Westlund, River Falls, WI (US); Donald F. Palme, II, Princeton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 406 days.

(21) Appl. No.: 10/971,577

(22) Filed: Oct. 22, 2004

(65) Prior Publication Data
US 2005/0119718 A1 Jun. 2, 2005

Related U.S. Application Data

(60) Provisional application No. 60/514,037, filed on Oct. 24, 2003, provisional application No. 60/514,665, filed on Oct. 27, 2003, provisional application No. 60/514,042, filed on Oct. 24, 2003, provisional application No. 60/514,714, filed on Oct. 27, 2003, provisional application No. 60/514,039, filed on Oct. 24, 2003, provisional application No. 60/514,146, filed on Oct. 24, 2003, provisional application No. 60/514,038, filed on Oct. 24, 2003, provisional application No. 60/514,713, filed on Oct. 27, 2003.

(51) Int. Cl.
*A61N 1/05* (2006.01)
(52) U.S. Cl. ........................ 607/120; 607/126
(58) Field of Classification Search .................. 607/120
See application file for complete search history.

(56) References Cited

U.S. PATENT DOCUMENTS

| 3,244,174 A | 4/1966 | Wesbey et al. |
| 3,474,791 A | 10/1969 | Bentov |
| 3,737,579 A | 6/1973 | Bolduc |
| 4,142,530 A | 3/1979 | Wittkampf |
| 4,161,952 A | 7/1979 | Kinney et al. |

(Continued)

FOREIGN PATENT DOCUMENTS

DE     2219044     11/1972

(Continued)

OTHER PUBLICATIONS

Assad et al., New Lead for In-Utero Pacing for Fetal Congenital Heart Block, Journal of Thoracic and Cardiovascular Surgery, Jul. 2003.

(Continued)

*Primary Examiner*—Carl H Layno
*Assistant Examiner*—Yun Haeng Lee
(74) *Attorney, Agent, or Firm*—Faegre & Benson LLP

(57) ABSTRACT

A myocardial lead attachment system for securing a distal end of a lead within a myocardium of a patient's heart. The system includes a lead body, an anchor mechanism formed of a bioabsorbable or biodegradable polymer for engaging a surface of the patient's heart and a surface feature formed on a portion of the lead body for promoting formation of scar tissue around said portion of the lead body.

21 Claims, 4 Drawing Sheets

U.S. PATENT DOCUMENTS

| | | | | |
|---|---|---|---|---|
| 4,258,724 | A | * | 3/1981 | Balat et al. .................. 607/128 |
| 4,341,226 | A | | 7/1982 | Peters |
| 4,355,642 | A | | 10/1982 | Alferness |
| 4,378,023 | A | | 3/1983 | Trabucco |
| 4,444,206 | A | * | 4/1984 | Gold .......................... 607/126 |
| 4,444,207 | A | | 4/1984 | Robicsek |
| 4,475,560 | A | * | 10/1984 | Tarjan et al. ................. 607/128 |
| 4,628,944 | A | * | 12/1986 | MacGregor et al. ......... 607/126 |
| 4,633,880 | A | | 1/1987 | Osypka et al. |
| 4,735,205 | A | | 4/1988 | Chachques et al. |
| 4,827,940 | A | * | 5/1989 | Mayer et al. ................ 600/375 |
| 4,991,578 | A | | 2/1991 | Cohen |
| 5,009,229 | A | | 4/1991 | Grandjean et al. |
| 5,217,027 | A | | 6/1993 | Hermens |
| 5,241,957 | A | | 9/1993 | Camps et al. |
| 5,300,107 | A | | 4/1994 | Stokes et al. |
| 5,314,462 | A | | 5/1994 | Heil et al. |
| 5,314,463 | A | | 5/1994 | Camps et al. |
| 5,318,543 | A | | 6/1994 | Ross et al. |
| 5,327,909 | A | | 7/1994 | Kiser et al. |
| 5,336,252 | A | | 8/1994 | Cohen |
| 5,350,419 | A | | 9/1994 | Bendel et al. |
| 5,385,579 | A | | 1/1995 | Helland |
| 5,423,876 | A | | 6/1995 | Camps et al. |
| 5,693,081 | A | | 12/1997 | Fain et al. |
| 5,716,392 | A | | 2/1998 | Bourgeois et al. |
| 5,755,767 | A | | 5/1998 | Doan et al. |
| 5,807,399 | A | | 9/1998 | Laske et al. |
| 5,836,994 | A | | 11/1998 | Bourgeois |
| 5,871,532 | A | | 2/1999 | Schroeppel |
| 6,041,258 | A | | 3/2000 | Cigaina et al. |
| 6,173,206 | B1 | | 1/2001 | Shchervinsky |
| 6,304,786 | B1 | * | 10/2001 | Heil et al. .................. 607/126 |
| 6,360,129 | B1 | * | 3/2002 | Ley et al. .................... 607/127 |
| 6,360,130 | B1 | | 3/2002 | Duysens et al. |
| 6,370,434 | B1 | | 4/2002 | Zhang et al. |
| 6,405,091 | B1 | | 6/2002 | Vachon et al. |
| 6,434,431 | B1 | | 8/2002 | Camps et al. |
| 6,459,937 | B1 | | 10/2002 | Morgan et al. |
| 6,473,654 | B1 | | 10/2002 | Chinn |
| 6,491,707 | B2 | | 12/2002 | Makower et al. |
| 6,510,332 | B1 | | 1/2003 | Greenstein |
| 6,512,958 | B1 | | 1/2003 | Swoyer et al. |
| 6,567,704 | B2 | | 5/2003 | Sundquist et al. |
| 6,613,062 | B1 | | 9/2003 | Leckrone et al. |
| 6,626,919 | B1 | | 9/2003 | Swanstrom |
| 6,671,553 | B1 | | 12/2003 | Helland et al. |
| 6,671,561 | B1 | | 12/2003 | Moaddeb |
| 6,842,648 | B2 | | 1/2005 | Partridge et al. |
| 6,941,174 | B2 | | 9/2005 | Shchervinsky |
| 2001/0000349 | A1 | | 4/2001 | Coe et al. |
| 2001/0039436 | A1 | | 11/2001 | Frazier et al. |
| 2002/0013571 | A1 | | 1/2002 | Goldfarb et al. |
| 2002/0072787 | A1 | | 6/2002 | Partridge |
| 2002/0077685 | A1 | | 6/2002 | Sundquist et al. |
| 2002/0123785 | A1 | | 9/2002 | Zhang et al. |
| 2002/0183818 | A1 | | 12/2002 | Williams et al. |
| 2003/0023295 | A1 | | 1/2003 | Osypka |
| 2003/0028232 | A1 | | 2/2003 | Camps et al. |
| 2003/0045919 | A1 | | 3/2003 | Swoyer et al. |
| 2003/0055463 | A1 | | 3/2003 | Gordon et al. |
| 2003/0125787 | A1 | | 7/2003 | Shchervinsky |
| 2003/0204231 | A1 | | 10/2003 | Hine et al. |
| 2004/0010282 | A1 | | 1/2004 | Kusleika |
| 2004/0015193 | A1 | * | 1/2004 | Lamson et al. ................. 607/9 |
| 2004/0260371 | A1 | | 12/2004 | Greenland et al. |
| 2005/0033394 | A1 | | 2/2005 | Seifert et al. |
| 2005/0033395 | A1 | | 2/2005 | Seifert et al. |
| 2005/0033396 | A1 | | 2/2005 | Osypka |
| 2005/0070986 | A1 | | 3/2005 | Tockman et al. |

FOREIGN PATENT DOCUMENTS

| | | |
|---|---|---|
| DE | 4425195 | 4/2003 |
| EP | 1000634 | 5/2000 |
| EP | 1025802 A | 8/2000 |
| GB | 2025236 A | 1/1980 |
| WO | 2004091716 | 10/2004 |
| WO | 2005028023 | 3/2005 |

OTHER PUBLICATIONS

Epstein et al., Long-Term Performance of Bipolar Epicardial Atrial Pacing Using an Active Fixation Bipolar Endocardial Lead, PACE, Apr. 1998.

Karpawich et al., Improved Epimyocardial Pacing, PACE, Nov. 1994.

Worley et al., Construction of a Multipolar Electrode System Referenced and Anchored to Endocardium for Study of Arrhythmias, American Physiological Society, 1986.

German Office Action citing prior art to related German Patent Application and English translation thereof.

Office Action received in related case U.S. Appl. No. 10/972,298, mailed Apr. 17, 2007.

Office Action received in related case U.S. Appl. No. 10/972,049, mailed Jul. 24, 2006.

Office Action received in related case U.S. Appl. No. 10/972,049, mailed Jan. 11, 2007.

Office Action received in related case U.S. Appl. No. 10/971,549, mailed Feb. 2, 2007.

Office Action received in related case U.S. Appl. No. 10/821,421, mailed May 25, 2006.

Office Action received in related case U.S. Appl. No. 10/821,421, mailed Nov. 24, 2006.

Office Action received in related case U.S. Appl. No. 10/821,421, mailed Mar. 22, 2007.

International Search Report and Written Opinion of International Application No. PCT/US2004/010907, filed Apr. 9, 2004, both mailed Sep. 16, 2004.

International Search Report and Written Opinion of International Application No. PCT/US2004/035172, filed Oct. 22, 2004, both mailed Jan. 31, 2005.

Office Action received in related case U.S. Appl. No. 10/971,549, mailed Jul. 27, 2007.

Office Action received in related case U.S. Appl. No. 10/972,049, mailed Jul. 2, 2007.

Agreement between Cardiac Pacemakers, Inc. and Dr. Osypka GmbH, dated Aug. 26, 2002, 2 pp.

* cited by examiner

ABSORBABLE MYOCARDIAL LEAD FIXATION SYSTEM

CROSS REFERENCES

The present application claims the benefit of the following U.S. Provisional Applications: Application Ser. No. 60/514,037 filed Oct. 24, 2003, entitled "Absorbable Myocardial Lead Fixation System", Application Ser. No. 60/514,665 filed Oct. 27, 2003, entitled "Lead Electrode Arrangement for Myocardial Leads", Application Ser. No. 60/514,042 filed Oct. 24, 2003, entitled "Tapered Tip for Myocardial Lead", Application Ser. No. 60/514,714 filed Oct. 27, 2003, entitled "Minimally-Invasive Fixation Systems for Over-the-Tether Myocardial Leads", Application Ser. No. 60/514,039 filed Oct. 24, 2003, entitled "Distal or Proximal Fixation of Over-the-Suture Myocardial Leads", Application Ser. No. 60/514,146 filed Oct. 24, 2003, entitled "Myocardial Lead with Fixation Mechanism", Application Ser. No. 60/514,038 filed Oct. 24, 2003, entitled "Delivery Instrument for Myocardial Lead Placement" and Application Ser. No. 60/514,713 filed Oct. 27, 2003, entitled "Drug-Eluting Myocardial Leads", all of which are incorporated herein by reference.

Reference is hereby made to the following commonly assigned U.S. patent application Ser. No. 10/821,421, filed Apr. 9, 2004 entitled "Cardiac Electrode Anchoring System" and the following commonly assigned U.S. patent applications filed on an even date herewith, all of which are incorporated herein by reference: application Ser. No. 10/972,049, entitled "Myocardial Lead", application Ser. No. 10/972,298, entitled "Distal or Proximal Fixation of Over-the-Tether Myocardial Leads", application Ser. No. 10/971,549, entitled "Myocardial Lead with Fixation Mechanism" and application Ser. No. 10/971,551, entitled "Myocardial Lead Attachment System."

PARTIES TO A JOINT RESEARCH AGREEMENT

The claimed invention was made subject to a joint research agreement between Cardiac Pacemakers, Inc. and Dr. Osypka, GmbH.

FIELD OF THE INVENTION

This invention relates generally to implantable lead assemblies for stimulating and/or sensing electrical signals in muscle tissue. More particularly, it relates to myocardially-implanted leads for cardiac stimulation and systems for anchoring and removing the leads.

BACKGROUND OF THE INVENTION

Cardiac rhythm management systems are used to treat heart arrhythmias. Pacemaker systems are commonly implanted in patients to treat bradycardia (i.e., abnormally slow heart rate). A pacemaker system includes an implantable pulse generator and leads which form the electrical connection between the implantable pulse generator and the heart. An implantable cardioverter defibrillator ("ICD") is used to treat tachycardia (i.e., abnormally rapid heart rate). An ICD also includes a pulse generator and leads that deliver electrical energy to the heart.

The leads coupling the pulse generator to the cardiac muscle are commonly used for delivering an electrical pulse to the cardiac muscle, for sensing electrical signals produced in the cardiac muscle, or for both delivering and sensing. The leads are susceptible to categorization according to the type of connection they form with the heart. An endocardial lead includes at least one electrode at or near its distal tip adapted to contact the endocardium (i.e., the tissue lining the inside of the heart). An epicardial lead includes at least one electrode at or near its distal tip adapted to contact the epicardium (i.e., the tissue lining the outside of the heart). Finally, a myocardial lead includes at least one electrode at or near its distal tip inserted into the heart muscle or myocardium (i.e., the muscle sandwiched between the endocardium and epicardium). Some leads have multiple spaced apart distal electrodes at differing polarities and are known as bipolar type leads. The spacing between the electrodes can affect lead performance and the quality of the electrical signal delivered or sensed through the heart tissue.

The lead typically includes a flexible conductor surrounded by an insulating tube or sheath that extends from the electrode at a distal end to a connector pin at a proximal end. Endocardial leads are typically delivered transvenously to the right atrium or ventricle and commonly employ tines at the distal end for engaging the trabeculae.

The treatment of congestive heart failure ("CHF"), however, often requires left ventricular stimulation either alone or in conjunction with right ventricular stimulation. For example, cardiac resynchronization therapy ("CRT") (also commonly referred to as biventricular pacing) is an emerging treatment for heart failure which requires stimulation of both the right and the left ventricle to increase cardiac output. Left ventricular stimulation requires placement of a lead in or on the left ventricle near the apex of the heart. One technique for left ventricular lead placement is to expose the heart by way of a thoracotomy. The lead is then positioned so that one or more electrodes contact the epicardium or are embedded in the myocardium. Another method is to advance an epicardial lead endovenously into the coronary sinus and then advance the lead through a lateral vein of the left ventricle. The electrodes are positioned to contact the epicardial surface of the left ventricle.

The left ventricle beats forcefully as it pumps oxygenated blood throughout the body. Repetitive beating of the heart, in combination with patient movement, can sometimes dislodge the lead from the myocardium. The electrodes may lose contact with the heart muscle, or spacing between electrodes may alter over time. It is also sometimes necessary to remove the leads. However, leads of the type described above can be difficult to remove.

There is a need therefore, for an improved myocardial lead system suitable both for chronic implantation and for later removal.

SUMMARY OF THE INVENTION

In one embodiment, the present invention is a myocardial lead attachment system for securing a distal end of a lead within a myocardium of a patient's heart. The system includes a lead body, an anchor mechanism coupled to the lead body for engaging the heart and a surface feature formed on a portion of the lead body. The anchor mechanism is formed of a bioabsorbable or biodegradable polymer. The surface feature promotes the formation of scar tissue around said portion of the lead body.

According to another embodiment, the present invention is a myocardial lead attachment system for securing a distal end of a lead within a myocardium of a patient's heart. The system includes a lead body coupled to an anchor mechanism for engaging the heart. The anchor mechanism is formed of a bioabsorbable or biodegradable polymer.

According to another embodiment, the present invention is a method for attaching a myocardial lead within the myocardium with an anchor mechanism. A dissolvable anchor mechanism coupled to a lead having a porous surface feature is inserted into the myocardium. Tissue is allowed to invade the porous surface feature and the anchor mechanism is allowed to dissolve.

This summary is not intended to describe each embodiment or every implementation of the present invention. Advantages and a more complete understanding of the invention will become apparent upon review of the detailed description and claims in conjunction with the accompanying drawings.

Figure 1:
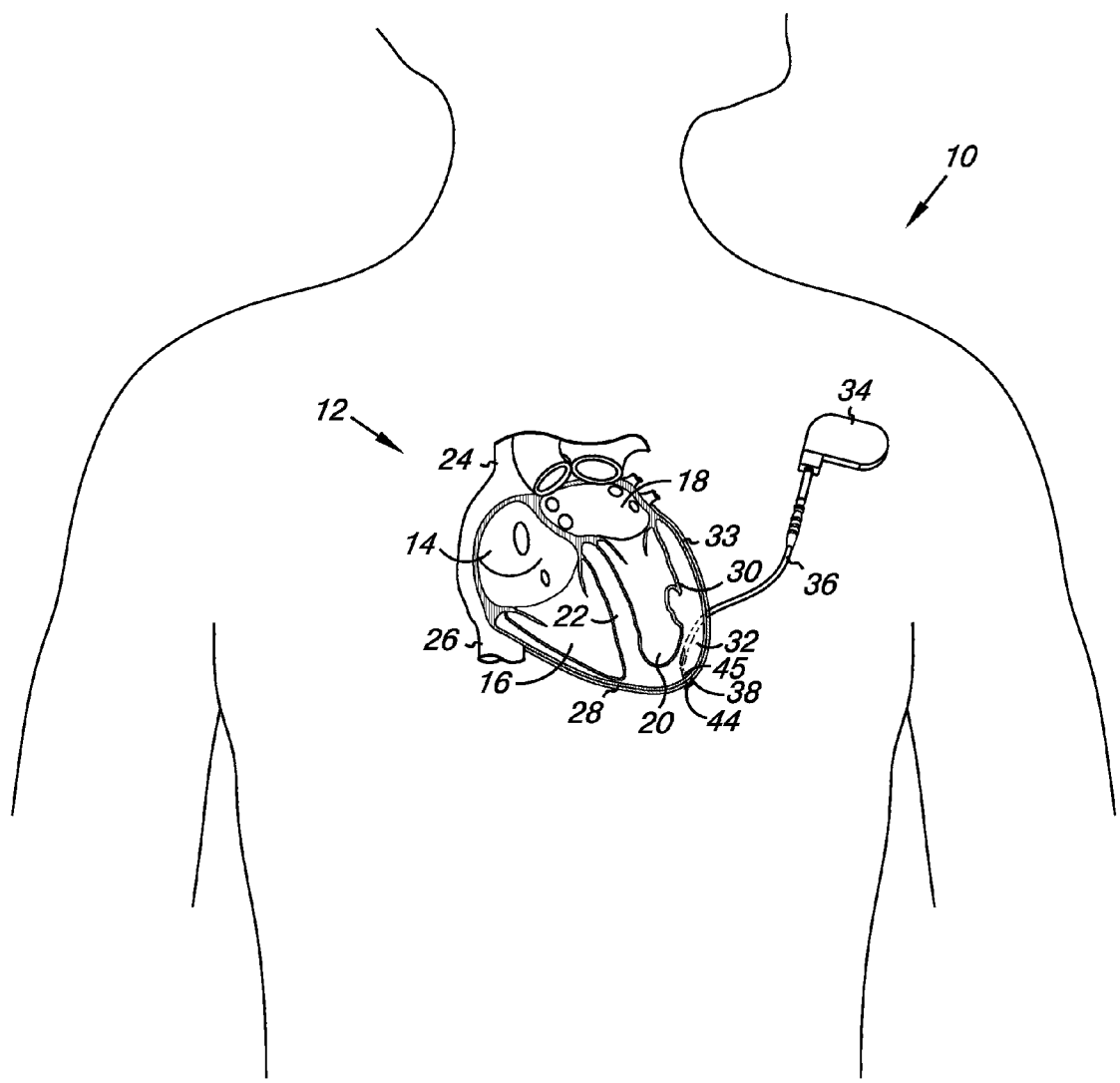
FIG. 1 is a sectional view of a portion of the vasculature and a myocardial lead attachment and pacing system according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a sectional view of a myocardial lead attachment and pacing system 10 deployed in a human heart 12 according to one embodiment of the present invention. As shown in FIG. 1, the heart 12 includes a right atrium 14 and a right ventricle 16 separated from a left atrium 18 and a left ventricle 20 by a septum 22. During normal operation of the heart 12, deoxygenated blood is fed into the right atrium 14 through the superior vena cava 24 and the inferior vena cava 26. The deoxygenated blood flows from the right atrium 14 into the right ventricle 16. The deoxygenated blood is pumped from the right ventricle 16 into the lungs, where the blood is re-oxygenated. From the lungs the oxygenated blood flows into the left atrium 18, then into the left ventricle 20. The left ventricle 20 beats forcefully to pump the oxygenated blood throughout the body.

The outer walls of the heart 12 are lined with a tissue known as the epicardium 28. The inner walls of the heart are lined with a tissue known as the endocardium 30. The heart muscle, or myocardium 32, is sandwiched between the endocardium 30 and the epicardium 28. A tough outer pericardial sac 33 surrounds the heart 12.

The myocardial lead attachment and pacing system 10 includes a pulse generator 34 coupled to a myocardial lead 36. The pulse generator 34 is typically implanted in a pocket formed underneath the skin of the patient's chest or abdominal region. The lead 36 extends from the pulse generator 34 to the heart 12 and is implanted in the myocardium 32 near an apex 38 of the heart 12. The lead 36 delivers electrical signals from the pulse generator 34 to an electrode positioned on the lead 36 to accomplish pacing of the heart 12 (not visible in FIG. 1).

An anchor mechanism 44 is coupled to the lead 36 via a tether 45 to secure the lead 36 to the heart 12 and to retain the electrode in a chosen location. The anchor mechanism 44 is made from any biocompatible material known in the art suitable for chronic implantation. The tether 45 is formed from any biocompatible material known in the art having a strength and flexibility sufficient to guide and secure the lead 36 within the myocardium 32. In one embodiment, the tether 45 is formed from any conventional suture material known in the art.

Placement of the lead 36 and anchor mechanism 44 in the heart 12 may be accomplished by exposing a portion of the heart 12, for example by way of a sternotomy, thoracotomy or mini-thoracotomy. According to other embodiments, the heart 12 may be accessed via an endoscopic procedure according to known methods. The lead 36 and anchor mechanism 44 are inserted through a tract in the heart 12 with the assistance of a delivery instrument. Suitable anchor mechanisms 44, delivery instruments and methods of implanting the anchor mechanism 44 and lead 36 are described in above-identified "Myocardial Lead Attachment System". The lead 36 is shown placed near the apex 38 of the heart 12. However, the lead 36 may be positioned in the heart 12 anywhere pacing therapy is needed.

In the embodiment shown in FIG. 1, the anchor mechanism 44 is configured to abut an epicardial surface. In other embodiments, the anchor mechanism 44 can be configured to abut an endocardial surface, a pericardial surface, or to be retained within the myocardium 32.

Over time, collagenous encapsulation tissue ("scar tissue") forms around the system 10. The formation of such scar tissue sometimes acts to secure the lead 36 in position.

According to one embodiment, the anchor mechanism 44 is made from a material formulated to dissolve or be absorbed over a period of time greater than a period of time necessary for the formation of scar tissue around the myocardial lead 36 following implantation. In one embodiment, the material is configured to dissolve in a period of time greater than a period of time necessary to secure the myocardial lead 36 to the myocardium 32 by scar tissue formation around the myocardial lead 36. Such material may be any bioabsorbable or biodegradable material, including, for example, polyglycolide ("PGA"), polylactide ("PLA"), polydioxanone ("PDA"), or polylactide-co-glycolide. In one embodiment, any combination of these polymers is used.

Dissolution or bioabsorption of the anchor mechanism 44 releases the tether 45 and lead 36. Although doing so reduces the level of fixation of the lead 36 within the myocardium 32, the lead 36 remains substantially secured within the myocardium 32 by epicardial and/or myocardial scar tissue. The lead 36 no longer need be detached from the anchor mechanism 44 prior to removal, as would otherwise be necessary. Rather, the lead 36 need only be separated from the surrounding scar tissue. Accordingly, this will facilitate later removal of the lead 36, if necessary.

In another embodiment, the material of the anchor mechanism 44 includes an agent, biologic material or drug, released as the anchor mechanism 44 dissolves, which would alter the local environment of the lead implantation site. This material could be selected to include anti-inflammatory material, angiogenic factors or cellular growth factors or modifiers to enhance healing and low stimulation thresholds.

In one embodiment, the tether 45 is made from any bioabsorbable or biodegradable material, such that a portion of the tether 45 located outside of the lead 36 dissolves or is absorbed over time. Such materials include, for example, PGA, PLA, PDA, or polylactide-co-glycolide as previously described. Dissolution of the tether 45 releases the lead 36 from the anchor mechanism 44. Again, the lead 36 then need only be separated from surrounding scar tissue prior to removal. The anchor mechanism 44 may be removed as well, or may remain in place, encapsulated by scar tissue. In one embodiment, both the anchor mechanism 44 and the tether 45 are made from a dissolvable or absorbable material.

Figure 2:
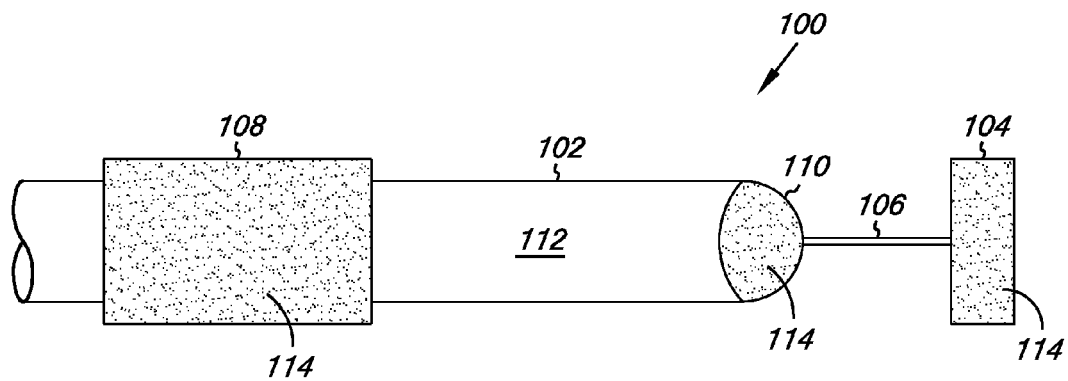
FIG. 2 is a side view of a distal portion of a myocardial lead attachment system according to one embodiment of the present invention.

FIG. 2 shows a side view of a distal portion of a myocardial lead attachment system 100 in accordance with another embodiment of the present invention. Attachment system 100 includes many of the same features as the system 10 shown in FIG. 1, including a lead 102, an anchor mechanism 104 and a tether 106 for securing the lead 102 within the myocardium 32. The lead 102 further includes a proximal electrode 108, a distal electrode 110 and an outer insulating sheath 112.

The system 100 is further provided with a porous or roughened surface feature(s) 114 into which collagenous encapsulation tissue ("scar tissue") invades, resulting in natural tissue anchoring. The scar tissue encapsulation that forms about the roughened surface feature(s) 114 provides a gripping action strengthened as the encapsulation tissue invades the surface feature(s) 114. Natural tissue anchoring strengthens the fixation between the lead 36 and the heart 12, reducing dislodgment and repositioning of the lead 102.

In the embodiment shown in FIG. 2, the proximal electrode 108, the distal electrode 110 and anchor mechanism 104 are provided with surface feature 114. According to other embodiments, portions of either or both of the proximal electrode 108 and distal electrode 110 in contact with heart tissue are provided with surface feature 114.

Putting surface feature 114 on the anchor mechanism 104 increases fixation of the anchor mechanism 104 to the heart 12 and reduces the likelihood of re-entry of the anchor mechanism 104 into the tract. According to other embodiments, either or both of the anchor mechanism 104 and the lead 102 include surface feature 114. In those embodiments in which the anchor mechanism 104 and/or tether 106 are dissolvable, as described above, the natural tissue anchoring improves lead fixation after either or both of the anchor mechanism 104 and tether 106 have dissolved.

Figure 3:
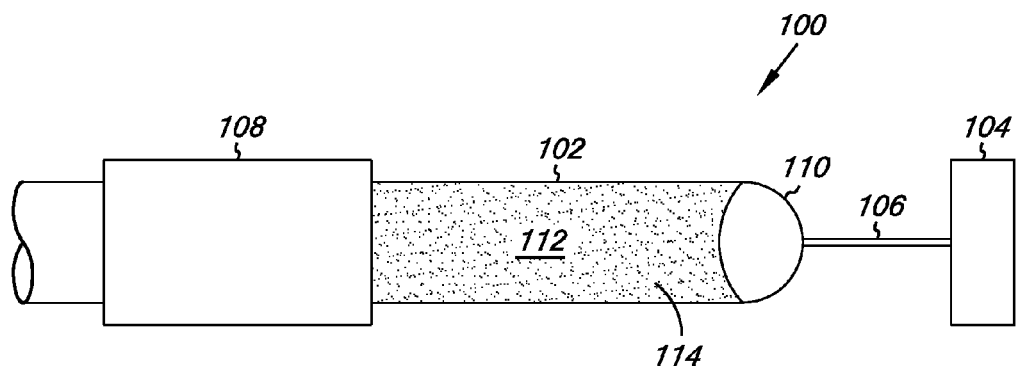
FIG. 3 is a side view of a distal portion of a myocardial lead attachment system according to another embodiment of the present invention.

FIG. 3 shows another embodiment in which the outer insulating sheath 112 is provided with surface feature 114. Any portion of the lead body 102 that passes through the epicardium 30 contains the surface feature 114. According to another embodiment, surface feature 114 is provided over the entire surface of the lead body 102 extending from the pulse generator 34 to the epicardium 30. Where the insulating sheath 112 is provided with surface feature 114, open channels that would provide electrical communication between internal conductor wires coupled to the proximal electrode 108 and distal electrode 110 (not visible in FIG. 2) and the myocardium 32 should be avoided.

Lead/electrode substrates forming a porous or roughened surface can be provided in a number of ways to form surface feature 114. In one example, the distal electrode 110, proximal electrode 108, sheath 112 or anchor mechanism 104 can be sand/grit blasted to bring about the surface feature 114. The rough or textured character of the surface feature 114 encourages tissue ingrowth. According to other embodiments, (not shown) circumferential grooves or other discontinuities form surface feature 114.

According to another embodiment, the distal electrode 110, proximal electrode 108 or anchor mechanism 104 can be fabricated from fused metallic particles so as to provide internal voids and channels forming surface feature 114 and into which tissue ingrowth takes place. According to another embodiment, the electrodes 108 and 110 or anchor mechanism 104 can be fabricated from metallic wire and/or screen mesh components that when compressed into an "electrode shape" create internal voids and channels to form surface feature 114.

Once tissue ingrowth has occurred, unwanted motion of the lead 102 relative to the heart 12 will be reduced or eliminated. In addition to reducing unwanted relative motion, a natural tissue anchoring feature such as that formed about surface feature 114 acts as a back-up anchor should the tether 106 primarily holding the lead body 102 in place stretch or break. Where either or both of the anchor mechanism 104 or tether 106 are intended to dissolve or be absorbed over time as discussed above, a natural tissue anchoring feature formed on the lead 102 improves lead 102 stability following dissolution or bioabsorption.

Figure 4:
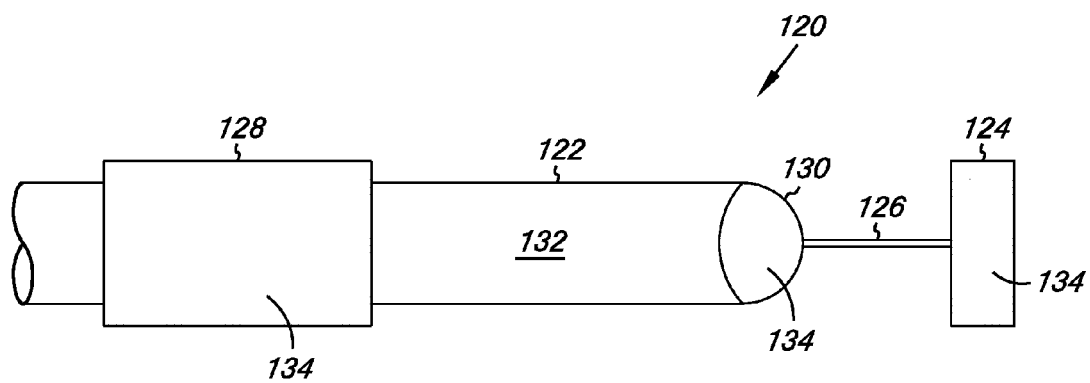
FIG. 4 is a side view of a distal portion of a myocardial lead attachment system according to yet another embodiment of the present invention.

FIG. 4 shows a side view of a distal portion of a myocardial lead attachment system 120 in accordance with another embodiment of the present invention. Attachment system 120 is generally similar to attachment system 100 shown in FIGS. 2 and 3 and includes a lead 122, an anchor mechanism 124 and a tether 126. The lead body 122 includes a proximal electrode 128, a distal electrode 130 and an outer insulating sheath 132. The proximal electrode 128 and distal electrode 130 are provided with a biocompatible conductive coating 134. The coating 134 may be formed with a smooth surface, as is shown in FIG. 4, or may be formed with a rough or porous surface as is previously described. The conductive coating 134 encourages growth and formation of the scar tissue, stabilizing the lead 120 within the myocardium 32.

Figure 5:
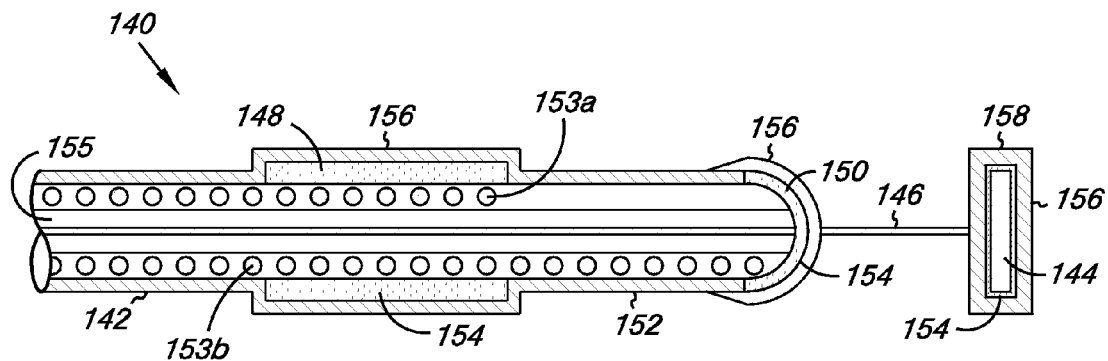
FIG. 5 is a side sectional view of a distal portion of a myocardial lead attachment system including a rapidly dissolvable coating according to another embodiment of the present invention.

FIG. 5 shows a distal portion of a myocardial lead attachment system 140 according to another embodiment of the present invention. The attachment system 140 is generally similar to that shown in FIG. 2 and includes a lead 142, an anchor mechanism 144 and a tether 146. The lead 142 includes a proximal electrode 148, a distal electrode 150 and an outer insulating sheath 152. Also shown are a pair of coiled conductive members 153a and 153b which are electrically coupled to the electrodes, 148 and 150, respectively. Also shown is a central lumen 155 extending through the lead 142 for receiving the tether 146. The lead 142 is provided with a roughened surface feature 154 formed on the proximal electrode 148, distal electrode 150 and/or anchor mechanism 144. A rapidly dissolvable outer coating 156 is formed over the surface feature 154. Such a rapidly dissolvable coating 156 may be formed of a material that is water soluble. The rapidly dissolvable coating 156 provides a smooth outer surface, masking any surface features, including roughened surface feature 154, to facilitate passage of the lead 142 and anchor mechanism 144 through the myocardium 32 during implantation. Following implantation, the coating 156 rapidly dissolves, revealing the surface features 154 to permit tissue ingrowth at the surface feature 154. According to other embodiments, the coating 156 is formed on the lead body 102 and/or anchor mechanism 144, or anywhere the surface feature 154 is formed.

Figure 6A:
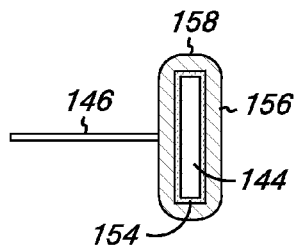
FIG. 6A is a side sectional view of the anchor mechanism of FIG. 5 including a rapidly dissolvable coating according to another embodiment of the present invention.

FIG. 6A shows another embodiment in which the rapidly dissolvable coating 156 has a first implant friendly shape or outer profile. Not only does the dissolvable coating 156 mask the roughened surface feature 154, as described above, the coating 156 forms a profile about the anchor mechanism 144 to facilitate implantation and passage through the myocardium 32. The coating 156 is smooth and has rounded edges chosen to reduce trauma to the myocardium 32 as the anchor mechanism 144 passes through the myocardial tissue 32 during insertion. Once the anchor mechanism 144 is in place, the coating 156 dissolves to expose the porous or roughened surface feature 154. According to other embodiments, the anchor mechanism 144 does not include a roughened surface feature 154, or is dissolvable as previously described.

Figure 6B:
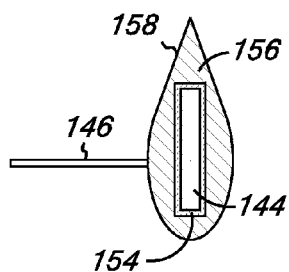
FIG. 6B is a side sectional view of the anchor mechanism of FIG. 5 according to yet another embodiment of the present invention.

FIG. 6B shows another embodiment in which the coating 156 is applied to the anchor mechanism 144 to generate a shape configured to facilitate tissue dissection. In the embodiment shown, coating 156 is shaped to form a sharp edge 158. An anchor mechanism 144 including this feature may be used in conjunction with a stylet delivery instrument as described in above-identified "Myocardial Lead Attachment System" to form a tract through the myocardium 32. Upon implantation, the coating 156 dissolves to expose the anchor mechanism 144.

Figure 7:
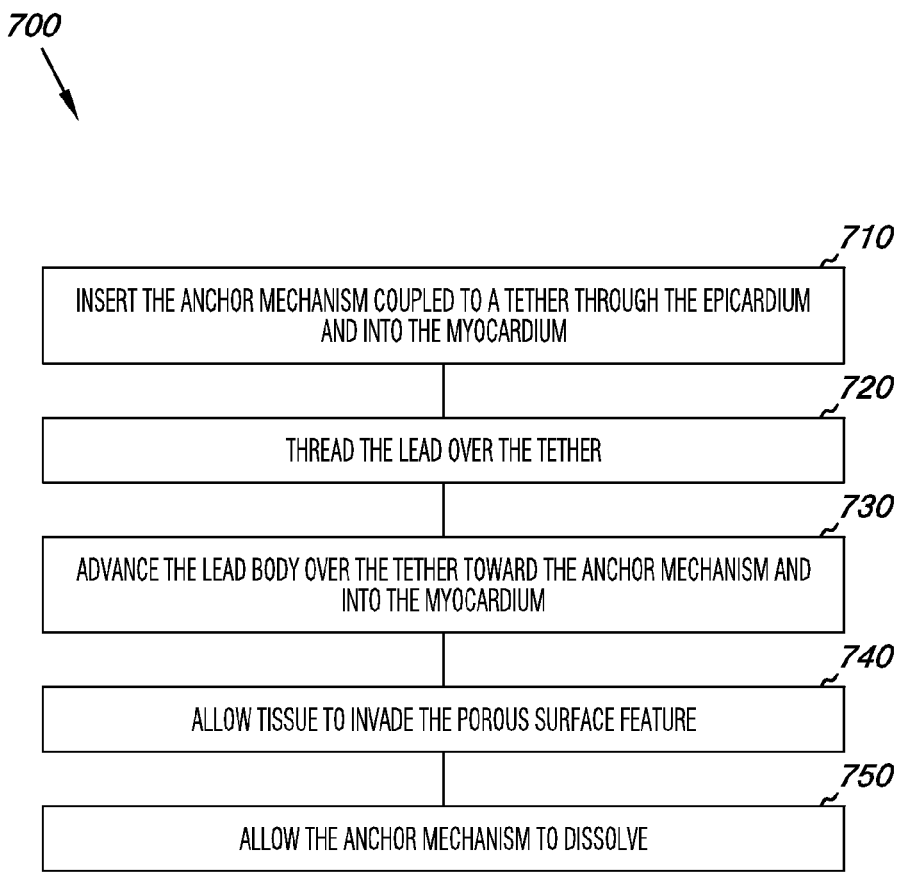
FIG. 7 is a flowchart depicting a method for attaching a myocardial lead within the myocardium with an anchor mechanism according to one embodiment of the present invention.

FIG. 7 is a flowchart depicting a method 700 for attaching a myocardial lead 142 having an anchor mechanism 144 within the myocardium 32 according to one embodiment of the present invention. An anchor mechanism 144 coupled to a tether 146 is inserted through the epicardium 28 and into the myocardium 32 (block 710). A lead 142 having a lead body 102, a lumen 155 for receiving the tether 146 extending through the lead 142, and a porous surface feature 154 formed on a portion of the lead body 102. The lead 142 is threaded over a proximal end of the tether 146 (block 720). The lead 142 is advanced over the tether 146 toward the anchor mechanism 144 and into the myocardium 32 (block 730). Tissue is allowed to invade the porous surface feature 154 (block 740). The anchor mechanism 144 is allowed to dissolve (block 750).

Various modifications and additions can be made to the exemplary embodiments discussed without departing from the scope of the present invention. Accordingly, the scope of the present invention is intended to embrace all such alternative, modifications, and variations as fall within the scope of the claims, together with all equivalents thereof.

We claim:

1. A myocardial lead attachment system for securing a distal end of a lead within a myocardium of a patient's heart, the system comprising:
    an anchor mechanism configured formed of a bioabsorbable or biodegradable polymer, the anchor mechanism configured to advance through myocardial tissue in a first orientation and configured to anchor against an epicardial surface in a second orientation;
    a tether having a proximal end and a distal end, wherein the anchor mechanism is coupled to the distal end of the tether; and
    a lead body having a proximal end, a distal end, a surface feature formed on a portion of the lead body for promoting formation of scar tissue around the portion, and a lumen extending through the lead body, wherein the lead body and the lumen are configured such that the lead body can be threaded over the proximal end of the tether and slideably advanced over the tether toward the anchor mechanism during implantation;
    wherein the anchor mechanism and the tether are configured to couple to the lead body, thereby chronically retaining the distal end of the lead body in the heart after implantation.

2. The system of claim 1 wherein the anchor mechanism is configured to dissolve after scar tissue forms around a portion of the lead body located within the myocardium.

3. The system of claim 1 wherein the anchor mechanism is made from a material selected from the group including: Polyglycolide ("PGA"), Polylactide ("PLA"), Polydioxanone ("PDA"), and Polylactide-co-glycolide.

4. The system of claim 1 wherein the anchor mechanism is made of a combination of bioabsorbable or biodegradable and non-bioabsorbable and non-biodegradable materials.

5. The system of claim 1 wherein the anchor mechanism further includes biologic or pharmacological agents in the bioabsorbable or biodegradable polymer that are released in order to modify the healing response to the lead placement.

6. The system of claim 1 wherein at least a portion of the tether is formed of a biodegradable or bioabsorbable polymer.

7. The system of claim 1 wherein the surface feature is a rough surface finish on the lead body.

8. The system of claim 1 wherein a portion of the lead body adapted to reside within the myocardium has the surface feature.

9. The system of claim 1 wherein substantially the entire lead body has the surface feature.

10. The system of claim 1 wherein the lead body further includes an electrode and wherein the surface feature is formed on at least a portion of the electrode.

11. The system of claim 10 wherein the surface feature is a conductive coating provided on the electrode.

12. The system of claim 10 wherein the surface feature is a rough surface finish on the electrode.

13. The system of claim 1 and further comprising a dissolvable coating applied over the surface feature.

14. The system of claim 13 wherein the dissolvable coating is water soluble.

15. The system of claim 13 wherein the dissolvable coating has a smooth outer surface.

16. The system of claim 1 and further comprising a dissolvable coating applied over the anchor mechanism, said coating having a trauma-reducing outer profile.

17. The system of claim 1 and further comprising a dissolvable coating applied over the anchor mechanism, said coating having a tissue-dissecting edge.

18. The myocardial lead attachment system of claim 1 wherein the first orientation of the anchor mechanism is substantially orthogonal to the second orientation of the anchor mechanism.

19. A myocardial lead attachment system for securing a distal end of a lead within a myocardium of a patient's heart, the system comprising:
    an anchor mechanism formed of a bioabsorbable or biodegradable polymer, the anchor mechanism configured to advance through myocardial tissue in a first orientation and configured to anchor against an epicardial surface in a second orientation;
    a tether having a proximal end and a distal end, wherein the anchor mechanism is coupled to the distal end of the tether; and a lead body having a proximal end, a distal end, and a lumen extending through the lead body, wherein the lead body and the lumen are configured such that the lead body can be threaded over the proximal end of the tether and slideably advanced over the tether toward the anchor mechanism during implantation;

wherein the anchor mechanism and the tether are configured to couple to the lead body, thereby chronically retaining the distal end of the lead body in the heart after implantation; and wherein the anchor mechanism is configured to dissolve after scar tissue forms around a portion of the lead body located within the myocardium.

20. A myocardial lead attachment system for securing a distal end of a lead within a myocardium of a patient's heart, the system comprising:

an anchor mechanism configured to advance through myocardial tissue in a first orientation and configured to anchor against an epicardial surface in a second orientation;

a tether having a proximal end and a distal end, wherein the anchor mechanism is coupled to the distal end of the tether; and a lead body having a proximal end, a distal end, a surface feature formed on a portion of the lead body for promoting formation of scar tissue around the portion, and a lumen extending through the lead body, wherein the lead body and the lumen are configured such that the lead body can be threaded over the proximal end of the tether and slideably advanced over the tether toward the anchor mechanism during implantation;

wherein the anchor mechanism and the tether are configured to couple to the lead body, thereby chronically retaining the distal end of the lead body in the heart after implantation.

21. The myocardial lead attachment system of claim 20 wherein first orientation of the anchor mechanism is substantially orthogonal to the second orientation of the anchor mechanism.

* * * * *